(12) United States Patent
Takeda

(10) Patent No.: US 11,842,808 B2
(45) Date of Patent: Dec. 12, 2023

(54) ULTRASOUND DIAGNOSTIC IMAGING TRAINING APPARATUS, ULTRASOUND DIAGNOSTIC IMAGING APPARATUS, IDENTIFICATION MODEL TRAINING METHOD, NON-TRANSITORY RECORDING MEDIUM STORING COMPUTER READABLE TRAINING PROGRAM, AND ULTRASOUND DIAGNOSTIC APPARATUS

(71) Applicant: Konica Minolta, Inc., Tokyo (JP)

(72) Inventor: Yoshihiro Takeda, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 442 days.

(21) Appl. No.: 17/038,454

(22) Filed: Sep. 30, 2020

(65) Prior Publication Data

US 2021/0103773 A1 Apr. 8, 2021

(30) Foreign Application Priority Data

Oct. 2, 2019 (JP) ................................ 2019-182469

(51) Int. Cl.
*A61B 8/08* (2006.01)
*A61B 8/14* (2006.01)
(Continued)

(52) U.S. Cl.
CPC ............. *G16H 30/40* (2018.01); *A61B 8/085* (2013.01); *A61B 8/0841* (2013.01); *A61B 8/14* (2013.01);
(Continued)

(58) Field of Classification Search
None
See application file for complete search history.

(56) References Cited

U.S. PATENT DOCUMENTS 10,817,753 B2 * 10/2020 Kudo .................... G06F 18/214
2019/0355149 A1 * 11/2019 Avendi ...................... G06T 7/74
(Continued)

FOREIGN PATENT DOCUMENTS

CN 112040896 A * 12/2020 ............. A61B 18/06
CN 112055569 A * 12/2020 ......... A61B 18/1492
(Continued)

OTHER PUBLICATIONS

Office Action dated May 9, 2023 for the corresponding Japanese Patent Application No. 2019-182469, with English translation.
(Continued)

*Primary Examiner* — Mohammed Rachedine
(74) *Attorney, Agent, or Firm* — LUCAS & MERCANTI, LLP

(57) ABSTRACT

An ultrasound diagnostic imaging training apparatus for training an identification model to be used for identifying a target in an ultrasound image generated based on reflected ultrasound reflected from inside a subject includes a first hardware processor that extracts a first image from the ultrasound image used for training and generates teacher data in which a feature value of a second image included in the first image is associated with information relating to a likelihood of the target, the generation of the teacher data being based on the first image and preset reference data; and a second hardware processor that trains the identification model through machine learning using the teacher data.

20 Claims, 12 Drawing Sheets

(51) Int. Cl.
*A61B 8/00* (2006.01)
*G06F 18/214* (2023.01)
*G06F 18/28* (2023.01)
*G06F 18/40* (2023.01)
*G06N 20/00* (2019.01)
*G06V 10/22* (2022.01)
*G16H 30/40* (2018.01)
*G16H 30/20* (2018.01)
*G06V 10/56* (2022.01)
*G06V 10/764* (2022.01)
*G06V 10/772* (2022.01)
*G06V 10/774* (2022.01)

(52) U.S. Cl.
CPC .............. *A61B 8/463* (2013.01); *A61B 8/469* (2013.01); *G06F 18/214* (2023.01); *G06F 18/28* (2023.01); *G06F 18/40* (2023.01); *G06N 20/00* (2019.01); *G06V 10/235* (2022.01); *G06V 10/56* (2022.01); *G06V 10/764* (2022.01); *G06V 10/772* (2022.01); *G06V 10/774* (2022.01); *G16H 30/20* (2018.01); *G06V 2201/03* (2022.01)

(56) References Cited

U.S. PATENT DOCUMENTS

2020/0100770 A1* 4/2020 Noguchi ............. G01S 7/52042
2020/0160097 A1* 5/2020 Jaber ..................... G06T 7/0012

FOREIGN PATENT DOCUMENTS

| | | | | |
|---|---|---|---|---|
| CN | 111329554 B | * | 1/2021 | ........... A61B 17/155 |
| JP | 2014-138847 A | | 7/2014 | |
| JP | 2019-028887 A | | 2/2019 | |
| JP | 2019508072 A | | 3/2019 | |
| JP | 2019-525786 A | | 9/2019 | |
| WO | WO-2009051847 A1 | * | 4/2009 | ............... A61B 5/06 |
| WO | 2019/039050 A1 | | 2/2019 | |

OTHER PUBLICATIONS

Office Action dated Aug. 22, 2023 for the corresponding Japanese Patent Application No. 2019-182469, with English translation, 8 pages.

* cited by examiner

FIRST REFERENCE DATA (K × K)

SECOND REFERENCE DATA (K × K)

SECOND REFERENCE DATA (K × K)

ULTRASOUND DIAGNOSTIC IMAGING TRAINING APPARATUS, ULTRASOUND DIAGNOSTIC IMAGING APPARATUS, IDENTIFICATION MODEL TRAINING METHOD, NON-TRANSITORY RECORDING MEDIUM STORING COMPUTER READABLE TRAINING PROGRAM, AND ULTRASOUND DIAGNOSTIC APPARATUS

CROSS REFERENCE TO RELATED APPLICATIONS

This application is entitled to and claims the benefit of Japanese Patent Application No. 2019-182469, filed on Oct. 2, 2019, the disclosure of which including the specification, drawings and abstract is incorporated herein by reference in its entirety.

BACKGROUND

Technological Field

The present invention relates to an ultrasound diagnostic imaging training apparatus, an ultrasound diagnostic imaging apparatus, an identification model training method, a non-transitory recording medium storing a computer readable training program, and an ultrasound diagnostic apparatus for identifying a target by using an identification model trained through machine learning.

Description of Related Art

One known medical diagnostic imaging apparatus of the related art is an ultrasound diagnostic apparatus that transmits ultrasound to a subject, receives a reflected wave of the ultrasound, and performs predetermined signal processing on a reception signal to visualize the shape, condition, or behavior of an object within the subject as an ultrasound image. The ultrasound diagnostic apparatus, which is capable of obtaining an ultrasound image with a simple operation such as applying an ultrasound probe to the surface of the body of the subject or inserting the ultrasound probe into the body of the subject, is safe and places less load on the subject.

The ultrasound diagnostic apparatus is used for the treatment of a target region under an ultrasound guide by, for example, inserting a treatment instrument (for example, a puncture needle) into the body of the subject. During the treatment, a practitioner such as a doctor can insert the treatment instrument and undergo the treatment while viewing the treatment target region in an ultrasound image obtained by the ultrasound diagnostic apparatus.

In the treatment under the ultrasound guide, it is desirable that the intended target region be clearly reflected in the ultrasound image (B-mode image) to accurately identify the location and extent of the treatment target region. For example, in a nerve block involving the injection of a local anesthetic directly into or near a peripheral nerve, a nerve into which the anesthetic agent is to be injected or a blood vessel or the like into which accidental injection of the anesthetic agent should be avoided may become a target. In the nerve block, the practitioner identifies nerves and blood vessels in an ultrasound image through individual visual inspection and pays attention to avoid accidental puncture of a blood vessel. The practitioner is thus required to be highly skilled and well experienced.

In recent years, a technique for identifying a target in an ultrasound image by using an identification model trained through machine learning and for providing the target to the user (for example, the practitioner) has also been proposed (see, for example, Japanese Unexamined Patent Application Publication (Translation of PCT Application) No. 2019-508072).

However, an ultrasound diagnostic apparatus disclosed in Japanese Unexamined Patent Application Publication (Translation of PCT Application) No. 2019-508072 requires the preparation of an accurate and enormous amount of training data (ground truth data) to train the identification model, and has a problem in that much labor and time are taken for, in particular, a user with less experience in training of the identification model to improve the performance (identification accuracy) of the identification model, which is inconvenient.

SUMMARY

It is an object of the present invention to provide an ultrasound diagnostic imaging training apparatus, an ultrasound diagnostic imaging apparatus, an identification model training method, a non-transitory recording medium storing a computer readable training program, and an ultrasound diagnostic apparatus that are capable of easily training an identification model through machine learning and accurately identifying a target in an ultrasound image to allow visual recognition.

To achieve at least one of the abovementioned objects, according to an aspect of the present invention, an ultrasound diagnostic imaging training apparatus reflecting one aspect of the present invention is an apparatus for training an identification model to be used for identifying a target in an ultrasound image generated based on reflected ultrasound reflected from inside a subject, the apparatus comprising:

a first hardware processor that extracts a first image from the ultrasound image used for training and generates teacher data in which a feature value of a second image included in the first image is associated with information relating to a likelihood of the target, the generation of the teacher data being based on the first image and preset reference data; and a second hardware processor that trains the identification model through machine learning using the teacher data.

An ultrasound diagnostic imaging apparatus reflecting one aspect of the present invention comprises:

the ultrasound diagnostic imaging training apparatus described above; and a third hardware processor that executes the identification model and outputs the information relating to the likelihood of the target in response to an input of a diagnostic ultrasound image.

An identification model training method reflecting one aspect of the present invention is a method for training an identification model to be used for identifying a target in an ultrasound image generated based on reflected ultrasound reflected from inside a subject, the identification model training method comprising:

extracting a first image from the ultrasound image used for training;

generating teacher data in which a feature value of a second image included in the first image is associated with information relating to a likelihood of the target, the generation of the teacher data being based on the first image and preset reference data; and training the identification model through machine learning using the teacher data.

A non-transitory recording medium reflecting one aspect of the present invention is a medium storing a computer readable training program for training an identification model to be used for identifying a target in an ultrasound image generated based on reflected ultrasound reflected from inside a subject, the training program causing a computer to perform:

extracting a first image from the ultrasound image used for training;
   generating teacher data in which a feature value of a second image included in the first image is associated with information relating to a likelihood of the target, the generation of the teacher data being based on the first image and preset reference data; and
   training the identification model through machine learning using the teacher data.

An ultrasound diagnostic apparatus reflecting one aspect of the present invention is an apparatus for generating and displaying an ultrasound image based on reflected ultrasound reflected from inside a subject, the ultrasound diagnostic apparatus comprising:

a fourth hardware processor that generates a B-mode image, the generation of the B-mode image being based on a reception signal corresponding to the reflected ultrasound;
   a fifth hardware processor that obtains information relating to a likelihood of a target in the B-mode image by using an identification model and generates a likelihood distribution for the B-mode image, the generation of the likelihood distribution being based on the information relating to the likelihood of the target, the identification model being trained in advance such that a likelihood for a region corresponding to the target becomes high and a likelihood for a structure other than the target becomes low; and
   a sixth hardware processor that displays a region corresponding to the target in the B-mode image in a visually recognizable manner by using the likelihood distribution.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

Figure 1:
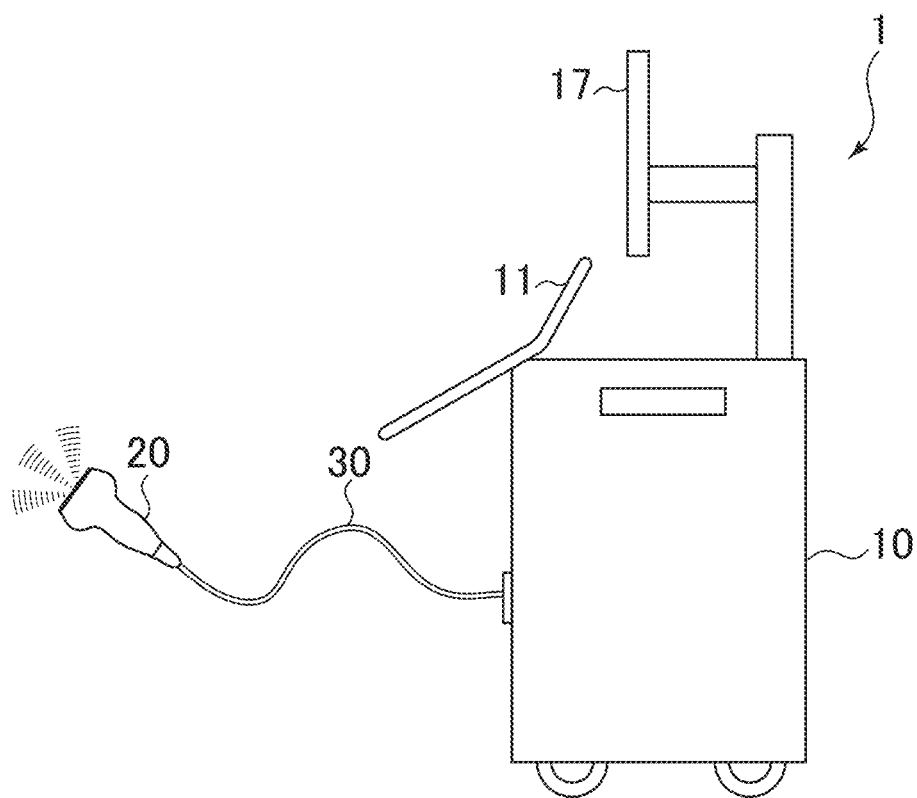
FIG. 1 is a diagram illustrating an external appearance of an ultrasound diagnostic apparatus according to an embodiment.
Figure 2:
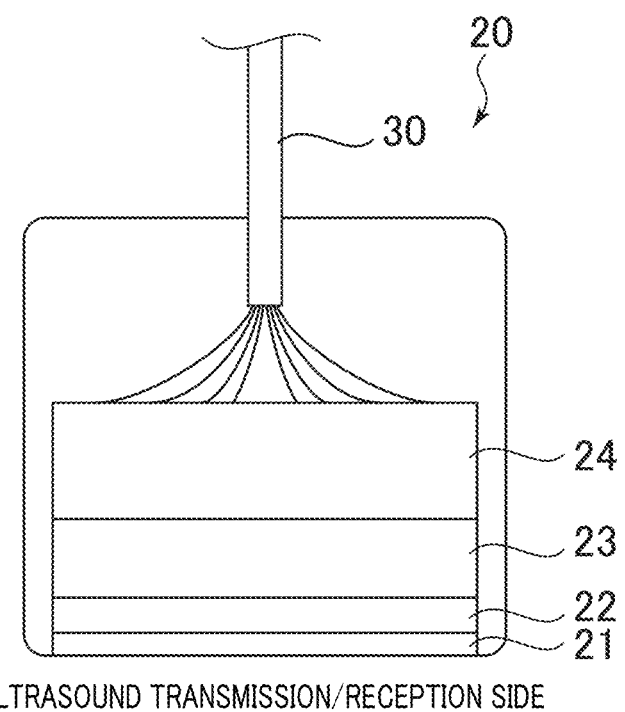
FIG. 2 is a diagram illustrating a configuration of an ultrasound probe.
Figure 3:
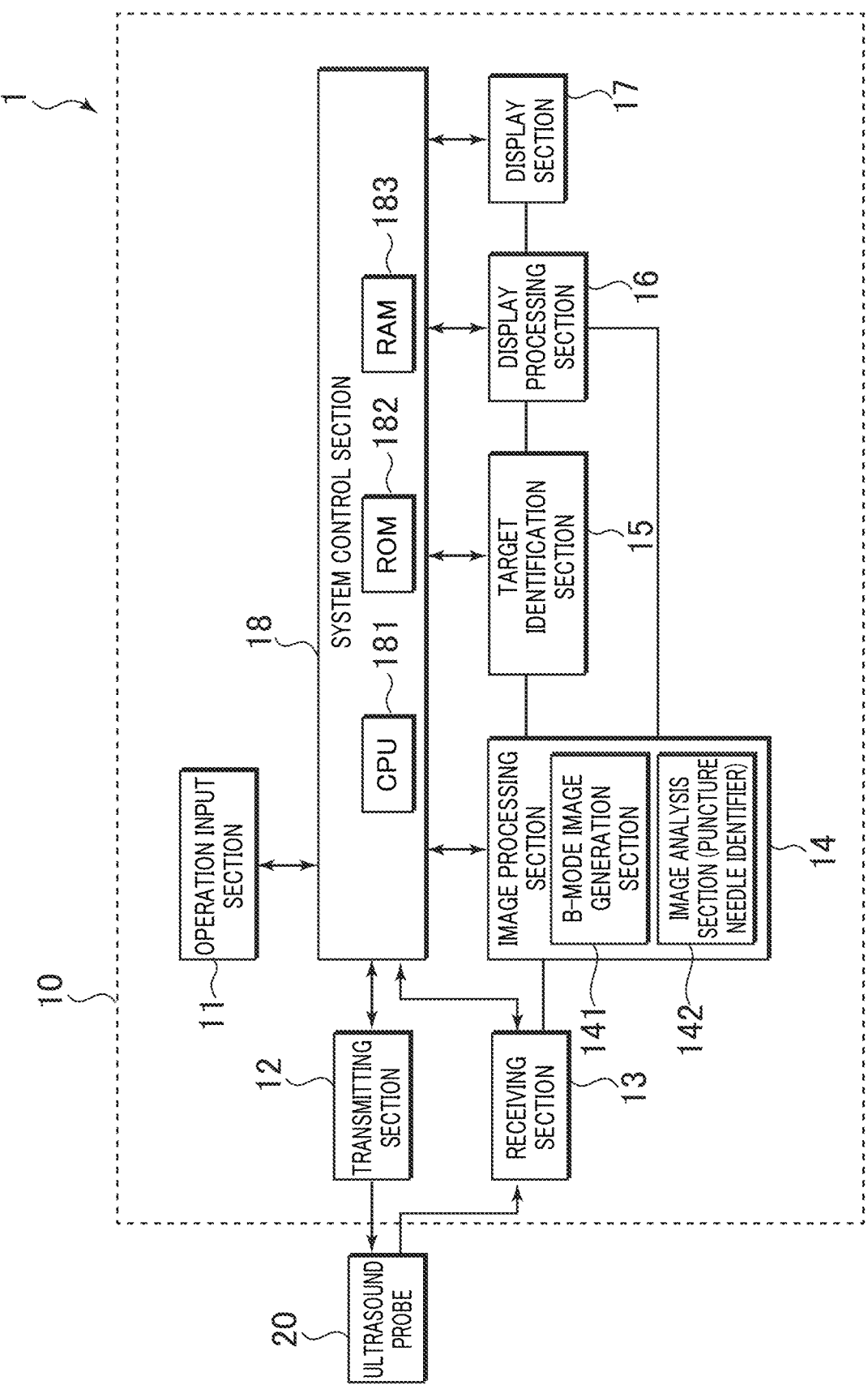
FIG. 3 is a block diagram illustrating a main part of a control system in the ultrasound diagnostic apparatus.

FIG. 1 is a diagram illustrating an external appearance of ultrasound diagnostic apparatus 1 according to an embodiment of the present invention. FIG. 2 is a diagram illustrating a configuration of ultrasound probe 20. FIG. 3 is a block diagram illustrating a main part of a control system in ultrasound diagnostic apparatus 1.

Ultrasound diagnostic apparatus 1 is used to visualize the shape, condition, or behavior of an object within a subject as an ultrasound image to perform diagnostic imaging Ultrasound diagnostic apparatus 1 has a function of presenting a target in a visually recognizable manner as puncture assistance information when, for example, a nerve block is performed on the subject by injecting an anesthetic agent into or around a nerve through puncture. In ultrasound diagnostic apparatus 1, a B-mode image shows a marker indicating a target to easily distinguish the target from a structure other than the target (the structure is hereinafter referred to as "non-target").

In a nerve block, for example, a nerve for determining a region into which the puncture needle is to be inserted, or a blood vessel that should not be confused with a nerve may become a target. In this embodiment, a nerve is handled as a target, and structures other than the nerve, such as blood vessels, bones, and muscle fibers, are handled as non-targets. When the anesthetic agent is to be injected around a nerve, the nerve and blood vessels into which the puncture needle should not be inserted may be handled as targets, and the other structures may be handled as non-targets.

As illustrated in FIG. 1, ultrasound diagnostic apparatus 1 includes ultrasound diagnostic apparatus body 10 and ultrasound probe 20. Ultrasound diagnostic apparatus body 10 and ultrasound probe 20 are connected via cable 30. Ultrasound probe 20 may be connected to ultrasound diagnostic apparatus body 10 via wireless communication.

Ultrasound probe 20 transmits ultrasound to a subject, receives an ultrasound echo (reflected ultrasound) reflected by the subject, converts the ultrasound echo into a reception signal, and transmits the reception signal to ultrasound diagnostic apparatus body 10. Ultrasound probe 20 may be any electronic scanning probe such as a convex probe, a linear probe, or a sector probe, or a mechanical scanning probe such as a mechanical sector probe. Ultrasound probe 20 may include a puncture needle guide section to which a puncture needle is attached. The puncture needle guide section is used to guide the direction of puncture.

As illustrated in FIG. 2, ultrasound probe 20 includes, for example, acoustic lens 21, acoustic matching layer 22, transducer array 23, and backing material 24 in this order from the ultrasound transmission/reception side. Acoustic lens 21 may have a protective layer on a surface (ultrasound transmission/reception surface) thereof.

Acoustic lens 21 is a lens that converges ultrasound in a slice direction (perpendicular to a scanning direction in which a plurality of transducers are arrayed). For example, when acoustic lens 21 is made of a material through which sound travels at a lower velocity than through a living body, acoustic lens 21 typically has a semi-cylindrical shape whose center portion in the slice direction bulges.

Acoustic matching layer 22 is an intermediate substance for allowing ultrasound to efficiently enter the subject. Acoustic matching layer 22 matches acoustic impedance between the transducers (not illustrated) and the subject.

Transducer array 23 is constituted by, for example, a plurality of strip-shaped transducers arranged in a single row in the scanning direction. That is, ultrasound probe 20 is a so-called single-row probe.

Backing material 24 attenuates unwanted vibration generated by transducer array 23.

Ultrasound diagnostic apparatus body 10 visualizes the shape, condition, or behavior of an object within the subject as an ultrasound image (B-mode image) by using the reception signal from ultrasound probe 20.

As illustrated in FIG. 3, ultrasound diagnostic apparatus body 10 includes operation input section 11, transmitting section 12, receiving section 13, image processing section 14, target identification section 15, display processing section 16, display section 17, system control section 18, and so on.

Each of transmitting section 12, receiving section 13, image processing section 14, target identification section 15, and display processing section 16 is formed of, for example, a dedicated or general-purpose hardware component (electronic circuit) for the corresponding processing, such as a digital signal processor (DSP), an application-specific integrated circuit (ASIC), or a programmable logic device (PLD), and cooperates with system control section 18 to implement the corresponding function.

Operation input section 11 receives, for example, input of a command for providing an instruction to start diagnosis or input of information relating to the subject. Further, operation input section 11 receives a target designation operation for designating a target or a non-target during the training of identification model 40 (see FIG. 4). Operation input section 11 includes, for example, an operation panel having a plurality of input switches, a keyboard, a mouse, and so on. Operation input section 11 may be configured as a touch panel integrated with display section 17.

Transmitting section 12 generates a transmission signal (drive signal) and outputs the transmission signal to ultrasound probe 20 in accordance with an instruction from system control section 18. Although not illustrated, transmitting section 12 includes, for example, a clock generation circuit, a pulse generation circuit, a pulse width setting section, and a delay circuit.

The clock generation circuit generates a clock signal for determining the transmission timing or transmission frequency of a pulse signal. The pulse generation circuit generates a bipolar rectangular-wave pulse having a preset voltage amplitude in a predetermined cycle. The pulse width setting section sets a pulse width of rectangular-wave pulses to be output from the pulse generation circuit. The rectangular-wave pulses generated by the pulse generation circuit are separated into lines different for the respective transducers of ultrasound probe 20 before or after the rectangular-wave pulses are input to the pulse width setting section. The delay circuit delays the generated rectangular-wave pulses in accordance with the transmission timings for the respective transducers, and outputs the resulting rectangular-wave pulses to the respective transducers.

Receiving section 13 receives a reception signal from ultrasound probe 20 and outputs the reception signal to image processing section 14 in accordance with an instruction from system control section 18. Although not illustrated, receiving section 13 includes, for example, an amplifier, an analog-to-digital (A/D) conversion circuit, and a phasing addition circuit.

The amplifier amplifies reception signals corresponding to ultrasounds received by the respective transducers of ultrasound probe 20 with a predetermined amplification factor that is set in advance. The A/D conversion circuit converts the amplified reception signals into digital data at a predetermined sampling frequency. The phasing addition circuit provides delays to the A/D converted reception signals for the respective lines corresponding to the transducers to adjust the time phases of the reception signals and adds together the resulting reception signals (phasing addition).

Image processing section 14 includes B-mode image generation section 141 and image analysis section 142. Although not illustrated, image processing section 14 further includes a digital scan converter (DSC) that performs coordinate conversion and pixel interpolation in accordance with the type of ultrasound probe 20.

B-mode image generation section 141 (fourth hardware processor) generates a B-mode image based on the reception signal in accordance with an instruction from system control section 18. The B-mode image indicates the internal state of the subject. When the puncture needle is inserted into the subject, the puncture needle is shown in the B-mode image.

Image analysis section 142 analyzes the B-mode image to identify, for example, the puncture needle in the B-mode image, and obtains puncture needle information.

Target identification section 15 (fifth hardware processor) generates data for identifying a target (here, a nerve) in a B-mode image used during treatment by using identification model 40 (see FIG. 4) in accordance with an instruction from system control section 18. An ultrasound diagnostic imaging training apparatus and an ultrasound diagnostic imaging apparatus according to an embodiment of the present invention are applied to target identification section 15. The details of target identification section 15 will be described below.

Identification model 40 is built using, for example, supervised machine learning in which the relationship between a feature value (for example, luminance array) of the B-mode image and information relating to a target likelihood is trained as teacher data 60 (see FIG. 4) by using a known machine learning algorithm (so-called deep learning) such as a neural network.

The target likelihood is a measure of the likelihood of being a target. The target likelihood for the target and the surrounding region of the target is high, whereas the target likelihood for the non-target region is low. The information relating to the target likelihood, which is output from identification model 40, may be, for example, a target likelihood (likelihood value) for a pixel block at the center of the B-mode image input to identification model 40 or a distribution of target likelihoods (hereinafter referred to as "likelihood distribution") for the entire B-mode image input to identification model 40. Pixel blocks are a plurality of regions into which an image is divided, and each pixel block may be constituted by a pixel group having a plurality of pixels or may be constituted by a single pixel.

That is, in response to an input of a B-mode image used during treatment, identification model 40 outputs data from which the likelihood distribution is generated. In this embodiment, in response to an input of a B-mode image having a predetermined size (hereinafter referred to as "identification image"), identification model 40 calculates the target likelihood for the pixel block at the center of the identification image and outputs the target likelihood. The likelihood distribution for the B-mode image used during treatment is generated based on the output of identification model 40. The size of the identification image to be input to identification model 40 and the information to be output from identification model 40 may be set as desired.

Display processing section 16 (sixth hardware processor) combines data of the B-mode image generated by image processing section 14 with data of the likelihood distribution generated by target identification section 15 (likelihood distribution generation section 154 (see FIG. 4)), converts the resulting data into a display signal for display section 17, and outputs the display signal in accordance with an instruction from system control section 18. For example, display processing section 16 adds color information (hue, saturation, and lightness) to each pixel of the B-mode image on the basis of the likelihood distribution, changes at least one of the hue, saturation, and lightness of the B-mode image, and displays a resulting image.

Display section 17 is formed of, for example, a liquid crystal display, an organic electroluminescent (EL) display, a cathode-ray tube (CRT) display, or the like. Display section 17 displays an image based on the display signal from display processing section 16 in accordance with an instruction from system control section 18.

System control section 18 controls operation input section 11, transmitting section 12, receiving section 13, image processing section 14, target identification section 15, display processing section 16, and display section 17 in accordance with the respective functions to perform the overall control of ultrasound diagnostic apparatus 1.

System control section 18 includes central processing unit (CPU) 181, which serves as an arithmetic/control device, read only memory (ROM) 182 and random access memory (RAM) 183, which serve as a main memory device, and so on. ROM 182 stores a basic program and basic settings data. ROM 182 also stores a treatment assistance program, which is executed in a treatment mode. CPU 181 reads a program for the content of processing from ROM 182, loads the program into RAM 183, and executes the loaded program to perform centralized control of the operations of the respective functional blocks of ultrasound diagnostic apparatus body 10 (transmitting section 12, receiving section 13, image processing section 14, target identification section 15, display processing section 16, and display section 17).

In this embodiment, the functions of the respective functional blocks are implemented by cooperation between the hardware components constituting the respective functional blocks and system control section 18. Some or all of the functions of the respective functional blocks may be implemented by system control section 18 executing programs.

Figure 4:
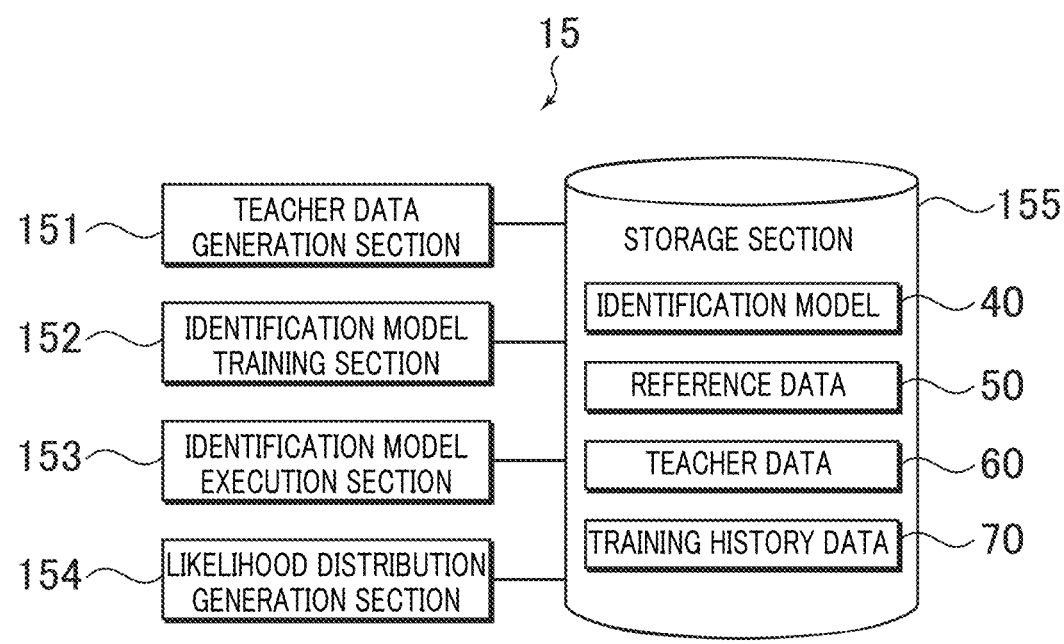
FIG. 4 is a diagram illustrating a specific configuration of a target identification section.

FIG. 4 is a diagram illustrating a specific configuration of target identification section 15.

As illustrated in FIG. 4, target identification section 15 includes, for example, teacher data generation section 151, identification model training section 152, identification model execution section 153, likelihood distribution generation section 154, and storage section 155.

Teacher data generation section 151 (first hardware processor) generates teacher data 60 for training identification model 40 on the basis of a first image for teacher data generation and reference data 50 prepared in advance. The first image is extracted from, for example, a B-mode image used for training Teacher data 60 is a data set in which a feature value (for example, luminance array) of a second image extracted from the first image and information relating to a target likelihood (for example, the target likelihood for the pixel block at the center of the second image) are associated with each other.

Identification model training section 152 (second hardware processor) trains identification model 40 through machine learning using teacher data 60 generated by teacher data generation section 151. Specifically, identification model training section 152 corrects identification model 40 so that when an example question of teacher data 60 (the feature value of the second image) is input to identification model 40, an answer of teacher data 60 (information relating to the target likelihood) is output.

Identification model execution section 153 (third hardware processor) executes trained identification model 40 and generates data for identifying a target in the B-mode image used during treatment. For example, identification model execution section 153 extracts identification image 92 from B-mode image 91 used during treatment and executes identification model 40 using identification image 92 as an input to obtain, as an output, information relating to the likelihood for identification image 92 (the target likelihood for the pixel block at the center of each identification image 92) (see FIG. 10).

Figure 10:
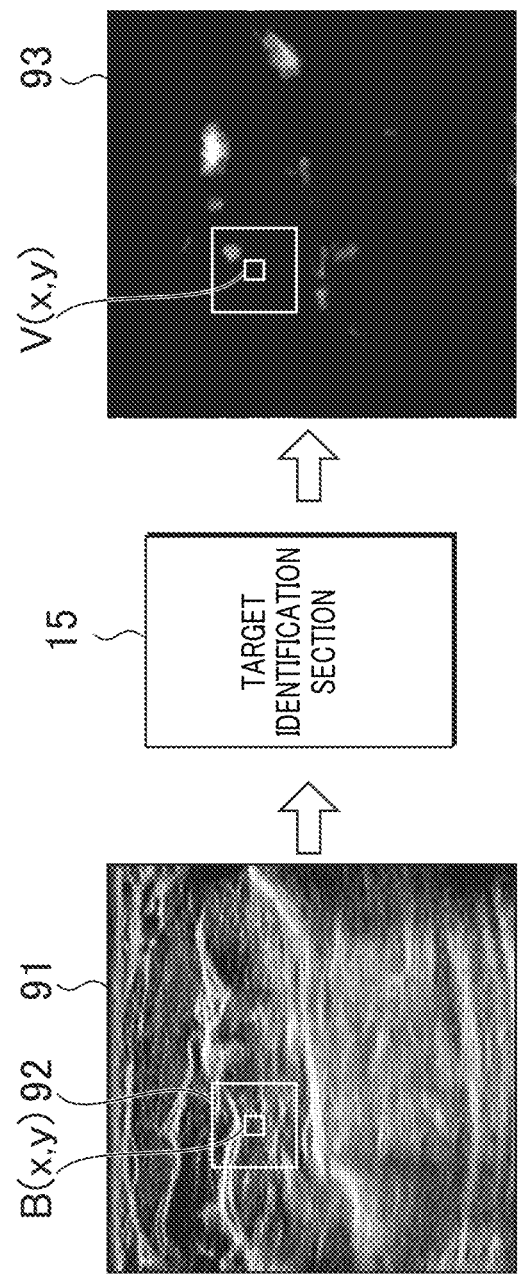
FIG. 10 is a diagram illustrating an example of a B-mode image used during treatment and the corresponding likelihood distribution.

Likelihood distribution generation section 154 (fifth hardware processor) generates data indicating likelihood distribution 93 for the entirety or a part (for example, a region surrounded by a region of interest (ROI) frame) of B-mode image 91 used during treatment on the basis of the output of identification model execution section 153 (see FIG. 10). At this time, noise is preferably removed from the likelihood distribution in accordance with a change in information relating to likelihoods obtained from B-mode images consecutive in time (for example, target likelihoods or likelihood distributions). For example, a moving-average filter or a median filter can be applied in the time axis direction to remove noise from the likelihood distribution. In this case, a region for which the change (steepness) in the information relating to the likelihoods exceeds a preset threshold may be detected as a noise region, and noise removal processing may be performed only on the noise region.

Storage section 155 is formed of, for example, a non-volatile semiconductor memory (a so-called flash memory), a hard disk drive, or the like. Storage section 155 may be a disk drive that drives an optical disk, such as a compact disc (CD), a digital versatile disc (DVD), or a Blu-ray Disc (BD) ("Blu-ray" is a registered trademark), or a magneto-optical disk, such as a magneto-optical (MO) disk, to read or write information.

Storage section 155 stores, for example, identification model 40, reference data 50, and teacher data 60. Teacher data 60, which is used for training identification model 40, may be overwritten with new teacher data 60, as necessary, when the new teacher data 60 is generated by teacher data generation section 151. Further, storage section 155 functions as a training history storage section and stores training history data 70. Training history data 70 includes, for example, information such as the number of pieces of teacher data 60 used for training and the date and time of training.

Figure 5A:
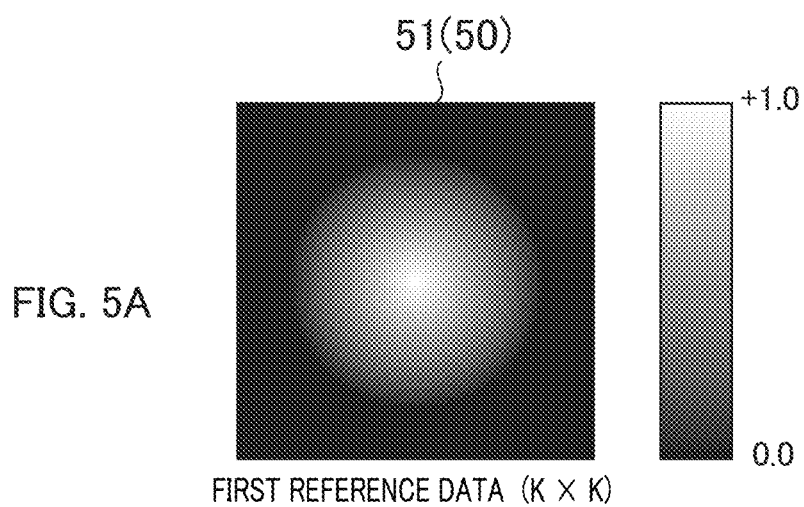
FIGS. 5A to 5C are diagrams illustrating examples of reference data.
Figure 5B:
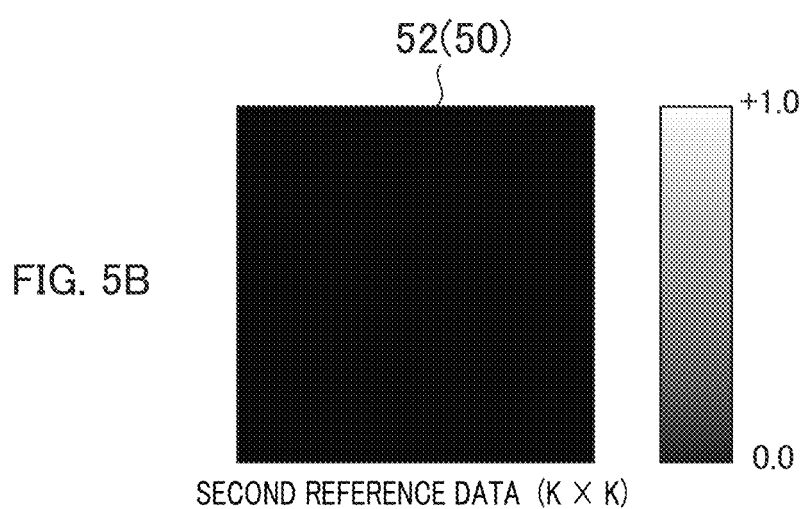
Figure 5C:
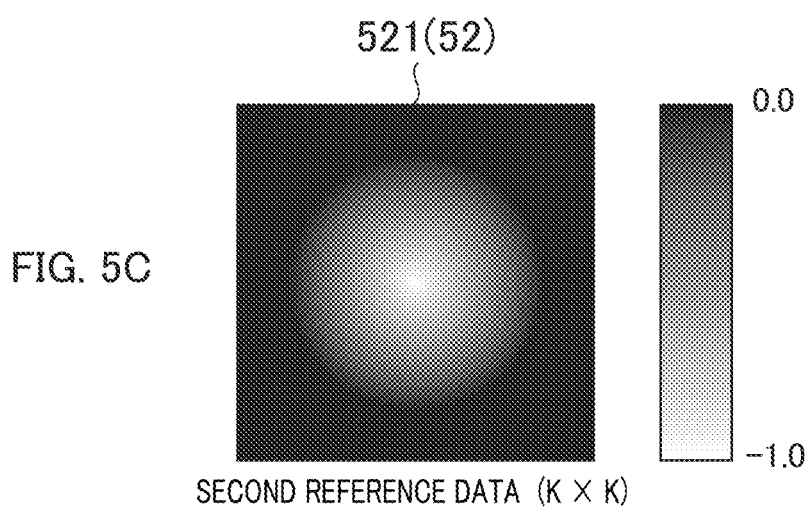

FIGS. 5A to 5C are diagrams illustrating examples of reference data 50.

As illustrated in FIGS. 5A to 5C, reference data 50 includes first reference data 51, which is referenced when the first image (teacher data generation B-mode image) includes a target, and second reference data 52, which is referenced when the first image includes no target.

First reference data 51 illustrated in FIG. 5A is referenced when a cross section of the target nerve is shown at the center of the first image. In first reference data 51, for example, the target likelihood is set in the range of 0.0 to 1.0 in accordance with a circular Gaussian distribution. Typically, a cross section of the nerve is shown in a B-mode image to be used in the nerve block and is used as a marker for determining a region into which the puncture needle is to be inserted.

Second reference data 52 indicates a likelihood distribution when the first image does not include the target nerve (when the first image includes a non-target structure). In second reference data 52 illustrated in FIG. 5B, the target likelihood for the entire region is set to 0.

A plurality of pieces of first reference data 51 and a plurality of pieces of second reference data 52 may be prepared, as necessary. For example, data to be referenced when a longitudinal section of the nerve is shown in the first image may be prepared as first reference data 51. Alternatively, as illustrated in FIG. 5C, second reference data 521 for identifying blood vessels, which is referenced when the first image includes a blood vessel into which the puncture needle should not be inserted, may be prepared as second reference data 52. Second reference data 521 for identifying blood vessels is referenced when a cross section of a blood vessel is shown at the center of the first image, and the target likelihood is set in the range of −1.0 to 0.0 in accordance with a circular Gaussian distribution.

Figure 6:
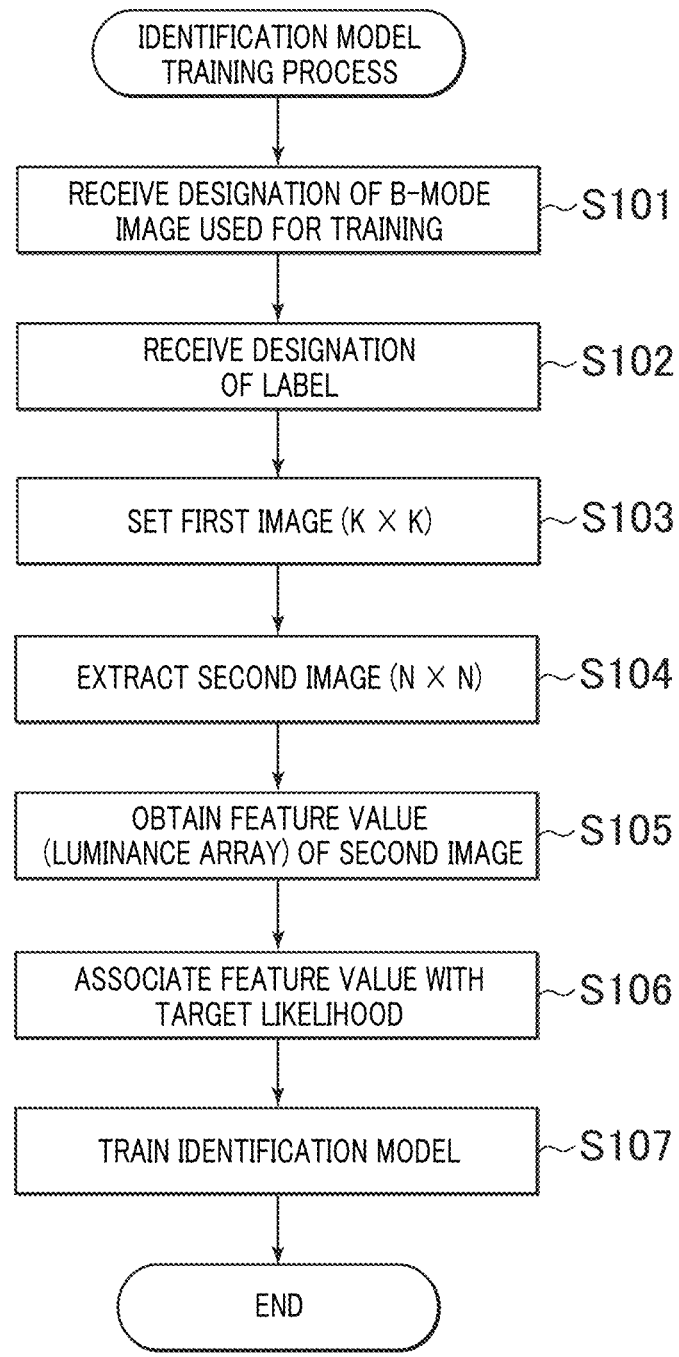
FIG. 6 is a flowchart illustrating an example of an identification model training process for training an identification model.

FIG. 6 is a flowchart illustrating an example of an identification model training process for training identification model 40. This process is implemented by, for example, CPU 181 executing a predetermined program (identification model training program) stored in ROM 182 in response to enabling of the training mode of identification model 40 in ultrasound diagnostic apparatus 1, in cooperation with teacher data generation section 151 and identification model training section 152. The enabling of the training mode is performed by, for example, mode selection using operation input section 11.

In step S101, teacher data generation section 151 receives designation of B-mode image 80 used for training (see FIG. 7) in accordance with an instruction from system control section 18. For example, B-mode image 80 used for training is obtained in advance for training and is stored in storage section 155. B-mode image 80 used for training is read in accordance with an input operation performed by the user using operation input section 11. For example, B-mode image 80 used for training may be a B-mode image obtained during the previous treatment. In this case, B-mode image 80 used for training may include the puncture needle.

In step S102, teacher data generation section 151 receives designation of a label in accordance with an instruction from system control section 18. The label includes a first label, which is designated when the training object is a target, and a second label, which is designated when the training object is a non-target. Either label is selected in accordance with an input operation performed by the user using operation input section 11. When the first label is designated, teacher data 60 is generated by using first reference data 51. When the second label is designated, teacher data 60 is generated by using second reference data 52.

Figure 7:
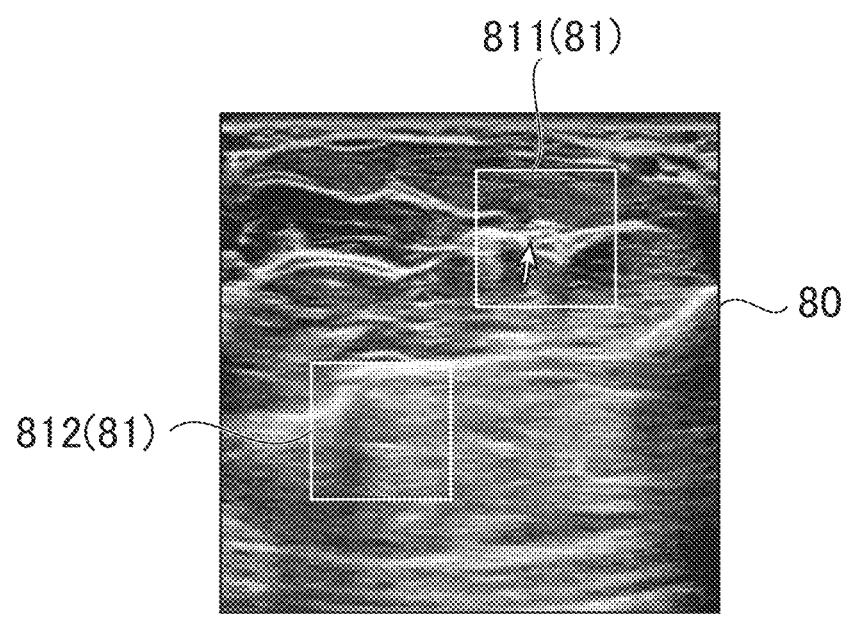
FIG. 7 is a diagram illustrating a B-mode image used for training and a first image.

In step S103, teacher data generation section 151 sets first image 81 in B-mode image 80 in accordance with an instruction from system control section 18 (see FIG. 7). In FIG. 7, an example of first image 811 and first image 812 are illustrated. First image 811 is set when the training object is a target, and first image 812 is set when the training object is a non-target.

First image 81 is set, for example, in accordance with a target designation operation performed by the user using operation input section 11. For example, when the user moves the cursor to a region where a target (or non-target) is shown in B-mode image 80 and then clicks, an area having a predetermined size centered on the region is set as first image 81. Alternatively, for example, the user may drag the cursor around a region where a target (or non-target) is shown in of B-mode image 80 to enlarge or shrink the rectangular frame, thereby designating a region to be set as first image 81.

First image 811, which is set when the training object is a target, preferably includes the puncture needle. Identification model 40 is trained by using teacher data 60 generated by using first image 811. This improves the performance of identifying a target for determining a region into which the puncture needle is to be inserted.

A specific description will hereinafter be given of a case where the first label is designated in step S102 and first image 811 including a target is set.

Figure 8A:
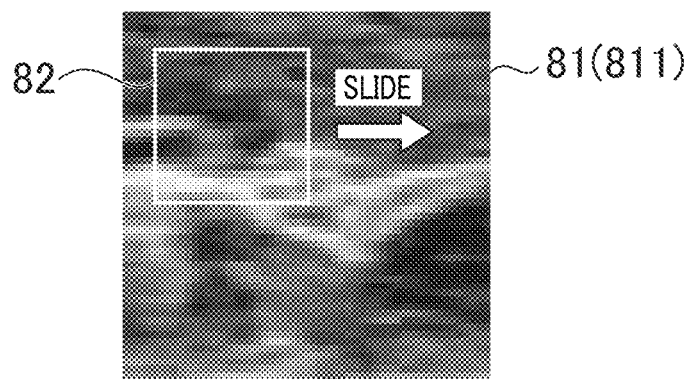
FIGS. 8A to 8C are diagrams illustrating an example method for generating teacher data.

In step S104, teacher data generation section 151 extracts second image 82 from first image 81 in accordance with an instruction from system control section 18 (see FIG. 8A). Second image 82 is an image that is included in first image 81 and that is an input (example question) of teacher data. For example, second image 82 constituted by a block of N×N pixels (N<M) is extracted from first image 81 constituted by a block of M×M pixels.

In step S105, teacher data generation section 151 obtain a feature value of second image 82 in accordance with an instruction from system control section 18. The feature value of second image 82 is, for example, a luminance array formed of luminance values of the respective pixels (or pixel blocks) of second image 82.

In step S106, teacher data generation section 151 associates the feature value of second image 82 with the target likelihood on the basis of reference data 50 in accordance with an instruction from system control section 18.

Figure 8B:
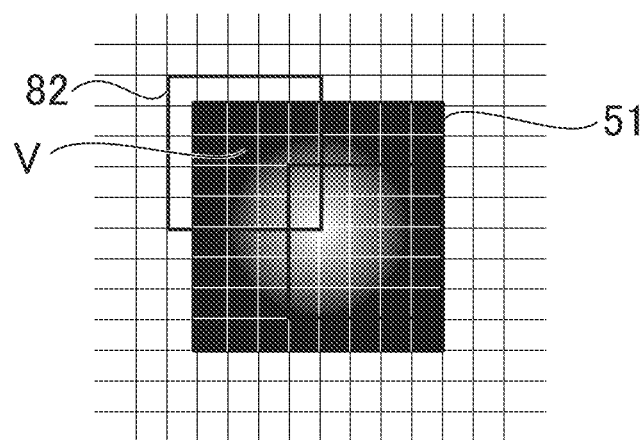

For example, as illustrated in FIGS. 8A and 8B, second image 82 is compared with first reference data 51, and target likelihood V for the pixel block at the center of second image 82 is determined from first reference data 51 and is associated with the feature value of second image 82. At this time, first reference data 51 is adjusted as desired in accordance with the size of first image 81.

Through the processing of step S106, a set of teacher data 60 in which the feature value of second image 82 and target likelihood V for the pixel block at the center of second image 82 are associated with each other is generated. The processing of steps S104 to S106 is performed while the region for extracting second image 82 is slid across first image 81. As a result, a plurality of sets of teacher data 60 are generated. For example, reference data 50 is constituted by a block of K×K pixels. In this case, target likelihoods can be assigned to feature values of (K×K) second images 82. That is, (K×K) pieces of teacher data can be generated merely by designating first image 81 once.

Teacher data generation section 151 executes the steps described above, thereby generating teacher data 60.

Figure 8C:
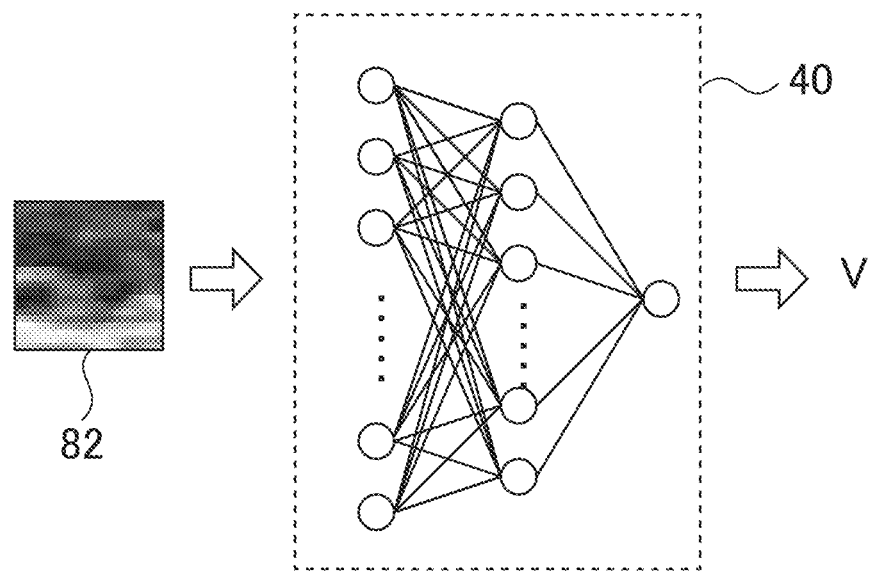

In step S107, identification model training section 152 trains identification model 40 through machine learning using the generated teacher data 60 in accordance with an instruction from system control section 18. Specifically, as illustrated in FIG. 8C, identification model training section 152 corrects identification model 40 so that when an example question of teacher data 60 (a feature value of second image 82) is input to identification model 40, an answer of teacher data 60 (target likelihood V for the pixel block at the center of second image 82) is output. Identification model 40 and training history data 70 stored in storage section 155 are updated in accordance with the result of the training.

When identification model 40 is trained, the training history of identification model 40 (for example, the number of pieces of teacher data that have been used for training) is preferably displayed on display section 17.

This allows the user to know the degree to which identification model 40 has been trained and to determine how much training will be required to obtain sufficient accuracy for target identification using identification model 40.

Figure 9:
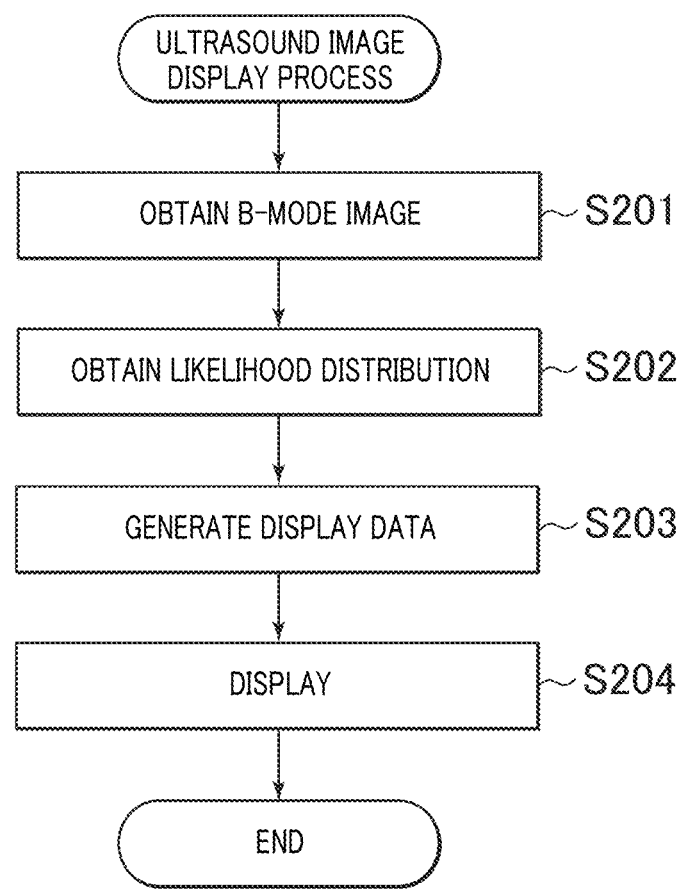
FIG. 9 is a flowchart illustrating an example of an ultrasound image display process when the ultrasound diagnostic apparatus is used for treatment with puncture.

FIG. 9 is a flowchart illustrating an example of an ultrasound image display process when ultrasound diagnostic apparatus 1 is used for treatment with puncture (for example, a nerve block). This process is implemented by, for example, CPU 181 executing a predetermined program (treatment assistance program) stored in ROM 182 in response to enabling of a puncture mode in ultrasound diagnostic apparatus 1. The enabling of the puncture mode is performed by, for example, mode selection using operation input section 11.

In step S201, system control section 18 obtains B-mode image 91 to be used for treatment (see FIG. 10). Specifically, system control section 18 controls transmitting section 12 to transmit ultrasound from ultrasound probe 20 and also controls receiving section 13 to obtain a reception signal corresponding to reflected ultrasound (ultrasound echo) received by ultrasound probe 20. Then, system control section 18 controls image processing section 14 (B-mode image generation section 141) to generate B-mode image 91, which is based on the reception signal.

In step S202, system control section 18 obtains likelihood distribution 93 for B-mode image 91 used during treatment (see FIG. 10). Specifically, system control section 18 controls target identification section 15 (identification model execution section 153) to extract identification image 92 from B-mode image 91 used during treatment, and executes identification model 40 using a feature value (for example, luminance array) of identification image 92 as an input. Then, as an output, target likelihood $V(x, y)$ for pixel block $B(x, y)$ at the center of identification image 92 is obtained. By executing identification model 40 while sliding the region for extracting identification image 92, target likelihoods for all the pixel blocks of B-mode image 91 are obtained. Then, system control section 18 controls target identification section 15 (likelihood distribution generation section 154) to generate data indicating likelihood distribution 93 for the entirety or a part (for example, a region surrounded by an ROI frame) of B-mode image 91 used during treatment on the basis of the output of identification model execution section 153.

B-mode image 91 used during treatment also shows the puncture needle inserted into the subject. Accordingly, when teacher data 60 for identification model 40 is to be generated, first image 81 preferably includes the target nerve and the puncture needle. This improves the performance of identifying a target for determining a region into which the puncture needle is to be inserted.

In step S203, system control section 18 controls display processing section 16 to generate display data on the basis of data of B-mode image 91 and data of likelihood distribution 93. For example, as illustrated in FIG. 11, system control section 18 sets the luminance and color (hue, saturation, and lightness) of each pixel of B-mode image 91 by using color map 94 with the vertical axis representing the luminance value of B-mode image 91 and the horizontal axis representing the target likelihood of likelihood distribution 93.

Figure 11:
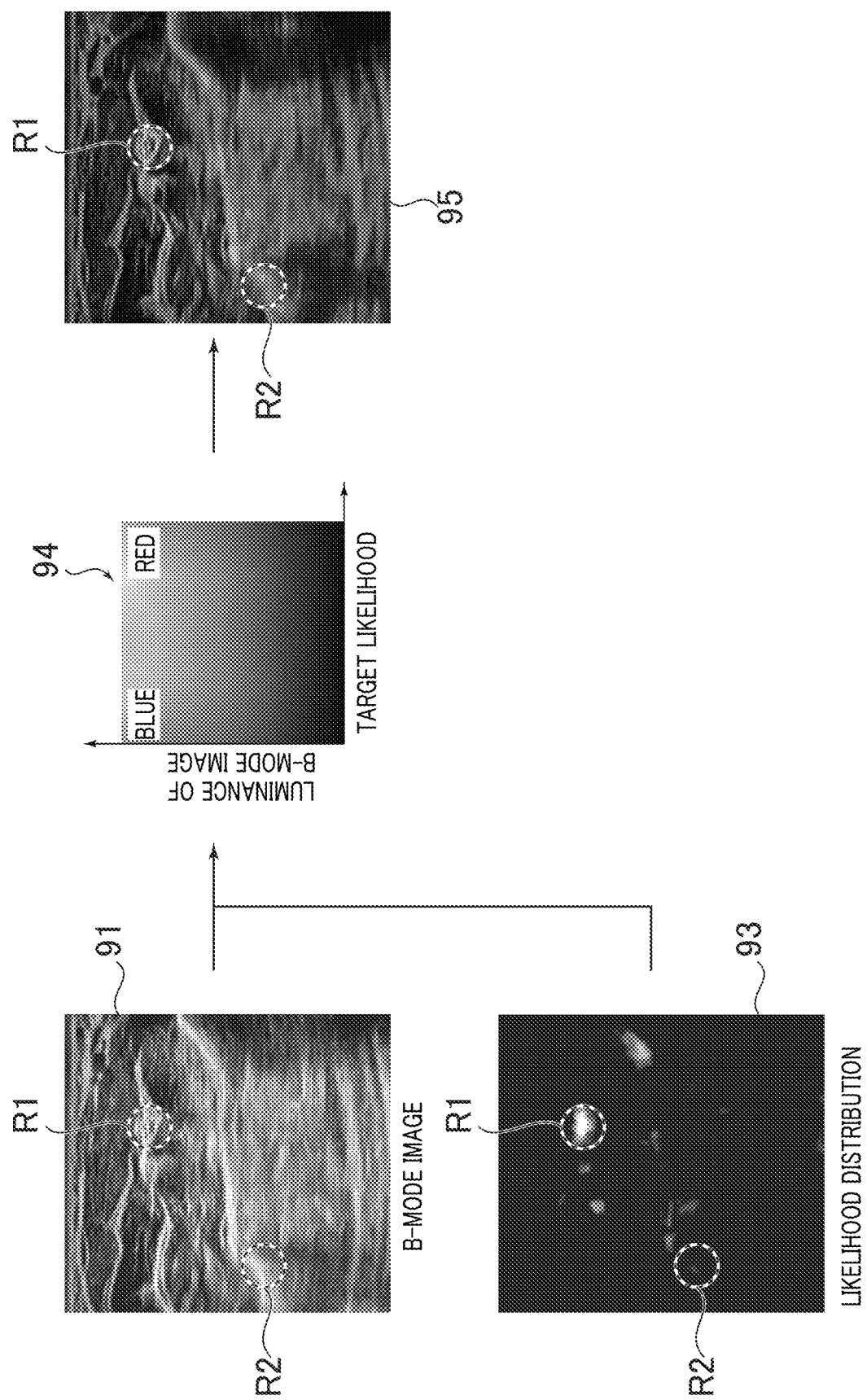
FIG. 11 is a diagram illustrating an example method for generating a display image based on a mode image and a likelihood distribution.

In step S204, system control section 18 controls display section 17 to display diagnostic display image 95 on the basis of the display data generated by display processing section 16 (see FIG. 11). In B-mode image 91, region R1 where the target nerve is shown has a high luminance value of B-mode image 91 and also has a high target likelihood. Accordingly, region R1 where the nerve is shown is displayed reddish in display image 95. In B-mode image 91, region R2 where a non-target structure (for example, a blood vessel) is shown has a relatively high luminance value of B-mode image 91 and a low target likelihood. Accordingly, region R2 is displayed bluish in display image 95.

The user is able to identify the target nerve from display image 95 generated on the basis of B-mode image 91 and likelihood distribution 93 for the target and to easily determine a region into which the puncture needle is to be inserted.

Display image 95 may be displayed in any manner so long as the target region in B-mode image 91 is displayed in a visually recognizable manner.

For example, in the processing of step S203, color map 94 may not be used, and a likelihood distribution image (not illustrated) that shows likelihood distribution 93 in color may be superimposed on B-mode image 91 to generate display data. Alternatively, B-mode image 91 and the likelihood distribution image may be displayed simply side by side.

For a non-target region for which the target likelihood is lower than a predetermined threshold in likelihood distribution 93, B-mode image 91 may be displayed as is without combining likelihood distribution 93 and B-mode image 91. This can prevent deterioration of the visual clarity of B-mode image 91 caused by combining B-mode image 91 and likelihood distribution 93, and can ensure the visibility of a non-target region irrelevant to the target nerve.

Figure 12A:
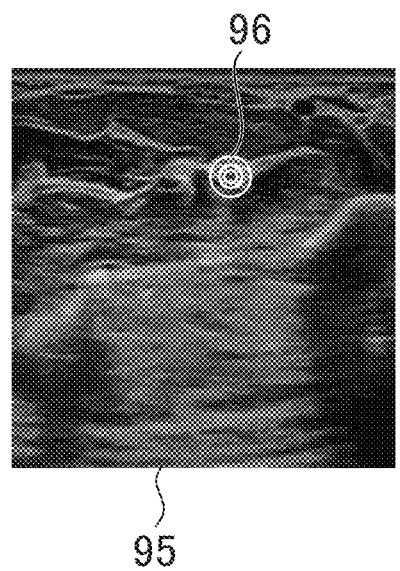
FIGS. 12A and 12B are diagrams illustrating other examples of the display image.
Figure 12B:
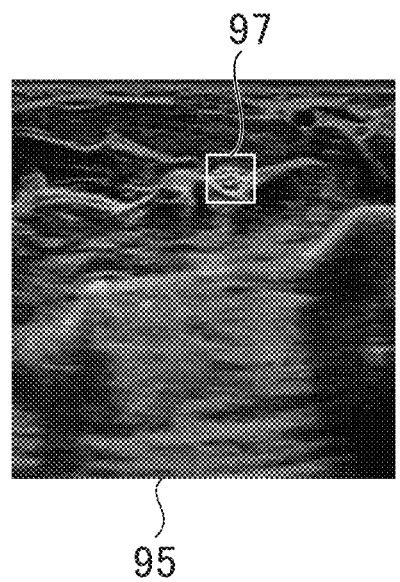

In addition, as illustrated in FIG. 12A, contour lines 96 based on likelihood distribution 93 may be superimposed on display image 95. Alternatively, as illustrated in FIG. 12B, target frame 97 based on likelihood distribution 93 may be superimposed on display image 95. The display of contour lines 96 or target frame 97 in display image 95 allows the user to more clearly identify the target region. Note that contour lines 96 or target frame 97 may be displayed in color display image 95 in which the likelihood distribution is reflected, or may be displayed in monochrome display image 95 (which is the same as original B-mode image 91) in which the likelihood distribution is not reflected.

As described above, target identification section 15 (ultrasound diagnostic imaging training apparatus) according to an embodiment is an ultrasound diagnostic imaging training apparatus for training identification model 40 to be used for identifying a target in an ultrasound image generated based on reflected ultrasound reflected from inside a subject, including teacher data generation section 151 that extracts first image 81 from B-mode image 80 (ultrasound image used for training) and that generates teacher data 60 in which a feature value of second image 82 included in first image 81 is associated with information relating to a likelihood of the target, the generation of teacher data 60 being based on first image 81 and preset reference data 50, and identification model training section 152 that trains identification model 40 through machine learning using teacher data 60.

Ultrasound diagnostic apparatus 1 according to an embodiment includes teacher data generation section 151 and identification model training section 152 (ultrasound diagnostic imaging training apparatus), and identification model execution section 153 that executes identification model 40 and outputs information relating to the likelihood of the target in response to an input of B-mode image 91 (diagnostic ultrasound image).

A method for training identification model 40 according to an embodiment is a method for training identification model 40 to be used for identifying a target in an ultrasound image generated based on reflected ultrasound reflected from inside a subject, including extracting (step S103 in FIG. 6) first image 81 from B-mode image 80 (ultrasound image used for training); generate (steps S104 to S106 in FIG. 6) teacher data 60 in which a feature value of second image 82 included in first image 81 is associated with information relating to a likelihood of the target, the generation of teacher data 60 being based on first image 81 and preset reference data 50; and training (step S107 in FIG. 6) identification model 40 through machine learning using teacher data 60.

A program according to an embodiment is a training program for training identification model 40 to be used for identifying a target in an ultrasound image generated based on reflected ultrasound reflected from inside a subject, and causes a computer to perform extracting (step S103 in FIG. 6) first image 81 from B-mode image 80 (ultrasound image used for training); generating (steps S104 to S106 in FIG. 6) teacher data 60 in which a feature value of second image 82 included in first image 81 is associated with information relating to a likelihood of the target, the generation of teacher data 60 being based on first image 81 and preset reference data 50; and training (step S107 in FIG. 6) the identification model through machine learning using teacher data 60.

The program is provided through, for example, a computer-readable portable storage medium (including an optical disk, a magneto-optical disk, and a memory card) storing the program. Alternatively, for example, the program may be provided by being downloaded via a network from a server that holds the program.

Target identification section 15 (ultrasound diagnostic imaging training apparatus), the method for training identification model 40, and the training program according to embodiments can easily train identification model 40 through machine learning and accurately identify a target in a B-mode image to allow visual recognition.

In particular, an enormous amount of teacher data 60 required for training identification model 40 can be generated for a short time through simple processing such as setting first image 81 from B-mode image 80 used for training and associating a label (target/non-target) with first image 81. Thus, even a user with less experience in training of identification model 40 can easily train identification model 40 to improve identification performance.

In target identification section 15 (ultrasound diagnostic imaging training apparatus), furthermore, teacher data generation section 151 sets a region for extracting first image 81 in accordance with an operation performed by a user to designate the target in B-mode image 80 (ultrasound image used for training).

Specifically, teacher data generation section 151 sets, as the region for extracting first image 81, a specific region centered on a position specified by coordinates of the target designated by the user.

With the configuration described above, teacher data 60 for training identification model 40 can be easily generated.

In target identification section 15 (ultrasound diagnostic imaging training apparatus), furthermore, reference data 50 includes first reference data 51 to be referenced when first image 81 includes the target, and second reference data 52 to be referenced when first image 81 is an image of a non-target other than the target.

Specifically, first reference data 51 includes a likelihood distribution in which a likelihood for a region corresponding to the target is set as a maximum likelihood and a likelihood for an object located at a larger distance from the target becomes lower, and in second reference data 52, a likelihood for a region corresponding to an entirety of first image 81 is 0.

With the configuration described above, identification model 40 can be trained so as to accurately identify a target and a non-target, and the identification performance of identification model 40 can be improved.

In target identification section 15 (ultrasound diagnostic imaging training apparatus), furthermore, the target is a nerve, and the non-target includes a blood vessel.

With the configuration described above, identification model 40 can reliably identify a nerve and a blood vessel that are difficult for a user to distinguish due to having similar structures. Accordingly, display image 25 is generated and displayed on the basis of the output of target identification section 15, thereby preventing the user from inserting the puncture needle into or around a blood vessel that is confused with a nerve. Thus, safety is improved.

In target identification section 15 (ultrasound diagnostic imaging training apparatus), furthermore, first image 81 includes a puncture needle inserted into or around a nerve.

With the configuration described above, the performance of identifying a target for determining a region into which the puncture needle is to be inserted is improved.

In target identification section 15 (ultrasound diagnostic imaging training apparatus), furthermore, first reference data 51 may be set for a plurality of targets.

With configuration described above, for example, a blood vessel or the like into which the puncture needle should not be inserted in a nerve block can also be set as a target. Thus, not only a region into which the puncture needle is to be inserted but also a region into which the puncture needle should not be inserted can be determined on the basis of the output of identification model 40.

In target identification section 15 (ultrasound diagnostic imaging training apparatus), furthermore, teacher data generation section 151 generates a plurality of sets of teacher data from single first image 81.

Specifically, teacher data generation section 151 references reference data 50 to calculate information relating to the likelihood of the target for each second image 82, and associates a feature value of second image 82 with a target likelihood for a pixel block at the center of second image 82.

With the configuration described above, an enormous amount of teacher data 60 required for training identification model 40 can be efficiently generated, and the identification performance of identification model 40 can be improved.

Target identification section 15 (ultrasound diagnostic imaging training apparatus) further includes storage section 155 (training history storage section) that stores a training history of identification model 40.

With the configuration described above, the training history of identification model 40 (for example, the number of pieces of teacher data used for training) can be presented. The user is able to know the degree to which identification model 40 has been trained, and is also able to determine how much training will be required to obtain sufficient accuracy for target identification using identification model 40.

Ultrasound diagnostic apparatus 1 according to embodiment is an ultrasound diagnostic apparatus for generating and displaying an ultrasound image based on reflected ultrasound reflected from inside a subject, including B-mode image generation section 141 that generates B-mode image 91 on the basis of a reception signal corresponding to the reflected ultrasound; target identification section 15 that obtains information relating to a likelihood of the target in B-mode image 91 by using identification model 40 and generates likelihood distribution 93 for B-mode image 91 on the basis of the information relating to the likelihood of the target, identification model 40 being trained in advance such that a likelihood for a region corresponding to the target becomes high and a likelihood for a structure other than the target becomes low; and display processing section 16 that displays a region corresponding to the target in B-mode image 91 in a visually recognizable manner by using likelihood distribution 93.

Ultrasound diagnostic apparatus 1 accurately identifies a target by using identification model 40 and displays a region corresponding to the target in B-mode image 91 in a visually recognizable manner. This allows the user to easily determine a marker to be used for treatment (for example, a nerve block).

In ultrasound diagnostic apparatus 1, the target is a nerve, the structure other than the target includes a blood vessel, and identification model 40 is trained in advance based on first reference data 51 including at least the nerve.

With the configuration described above, for example, when a nerve block is performed, a nerve serving as a marker for a region into which the puncture needle is to be inserted and a blood vessel into which the puncture needle should not be inserted can be presented to the user in a clearly distinguishable manner. This prevents the user from inserting the puncture needle into or around a blood vessel that is confused with the nerve. Thus, safety is improved.

In ultrasound diagnostic apparatus 1, display processing section 16 displays the region corresponding to the target in such a manner that at least one of the hue, saturation, and lightness of B-mode image 91 is changed in accordance with likelihood distribution 93.

Specifically, display processing section 16 displays B-mode image 91 and a likelihood distribution image (not illustrated) in which likelihood distribution 93 is displayed in color, in such a manner that the likelihood distribution image and B-mode image 91 are superimposed on each other.

With the configuration described above, the user is able to easily sense the presence of a target by using colors.

In ultrasound diagnostic apparatus 1, display processing section 16 displays a non-target region in B-mode image 91 without a change, the non-target region being a region for which a target likelihood is lower than a predetermined threshold in likelihood distribution 93.

The configuration described above can prevent deterioration of the visual clarity of B-mode image 91 caused by combining B-mode image 91 and likelihood distribution 93, and can ensure the visibility of display image 95.

In ultrasound diagnostic apparatus 1, furthermore, display processing section 16 displays contour lines 96 based on likelihood distribution 93 in such a manner as to be superimposed on B-mode image 91.

Alternatively, display processing section 16 displays target frame 97 based on likelihood distribution 93 in such a manner as to be superimposed on B-mode image 91.

With the configuration described above, the user is able to more clearly identify the region corresponding to the target.

In ultrasound diagnostic apparatus 1, likelihood distribution generation section 154 removes noise from likelihood distribution 93 in accordance with a change in information relating to the likelihood of the target over time.

Accordingly, smoothing of display image 25 in the time axis direction is achieved, and the visibility of the target is improved.

While an invention made by the present inventor has been described specifically with reference to embodiments, the present invention is not limited to the embodiments described above and may be changed without departing from the scope of the invention.

For example, in the embodiments, a target region is displayed in a visually recognizable manner on the basis of the likelihood distribution for the target. Alternatively, both the likelihood distribution for the target and puncture needle information indicating the puncture needle inserted into the subject may be utilized.

Specifically, ultrasound diagnostic apparatus 1 includes image analysis section 142 (puncture needle identifier) that obtains, from a B-mode image, puncture needle information indicating a puncture needle inserted into the subject, and display processing section 16 displays the region corresponding to the target in the B-mode image in a visually recognizable manner by using the puncture needle information and the likelihood distribution.

In this case, identification model 40 is trained in advance based on first reference data 51 including at least a nerve and the puncture needle.

Accordingly, a target for determining a region into which the puncture needle is inserted in the B-mode image can be accurately identified to allow visual recognition.

Display processing section 16 may display the puncture needle in the B-mode image in a highlighted manner.

With the configuration described above, the user is able to visually recognize the positional relationship between the puncture needle and the target nerve.

Alternatively, display processing section 16 may display the region corresponding to the target in such a manner that at least one of the hue, saturation, and lightness of the B-mode image is changed in accordance with the puncture needle information and the likelihood distribution.

Alternatively, display processing section 16 may display contour lines based on the likelihood distribution in such a manner as to be superimposed on the B-mode image and change a display style of the contour lines in accordance with the puncture needle information.

Alternatively, display processing section 16 may display a target frame based on the likelihood distribution in such a manner as to be superimposed on the B-mode image and change a display style of the target frame in accordance with the puncture needle information.

Specifically, the display style of a portion with a high target likelihood and/or a portion where the puncture needle is shown is changed in accordance with the positional relationship between the puncture needle and the nerve.

Accordingly, the user is able to easily determine the state of the inserted puncture needle.

In the embodiment, furthermore, since second image 82 is formed of a region included in first image 81, a plurality of sets of teacher data are generated from a single first image. Alternatively, second image 82 may be formed of an entire region of first image 81. In this case, a set of teacher data is generated from single first image 81.

In the embodiment, furthermore, a nerve is handled as a target, and a structure other than the nerve, including a blood vessel, is handled as a non-target. Alternatively, both a nerve and a blood vessel may be handled as targets.

Although embodiments of the present invention have been described and illustrated in detail, the disclosed embodiments are made for purpose of illustration and example only and not limitation. The scope of the present invention should be interpreted by terms of the appended claims.

What is claimed is:

1. An ultrasound diagnostic imaging training apparatus for training an identification model to be used for identifying a target in an ultrasound image generated based on reflected ultrasound reflected from inside a subject, the ultrasound diagnostic imaging training apparatus comprising:
    a first hardware processor that extracts a first image from the ultrasound image used for training and generates teacher data in which a feature value of a second image included in the first image is associated with information relating to a likelihood of the target, the generation of the teacher data being based on the first image and preset reference data, wherein the first image is extracted based on a user input that identifies a location of the first image in the ultrasound image and labels the first image as a target or a non-target, the preset reference data includes a first reference data that is used to determine the feature value when the first image is labeled as the target and a second reference data that is used to determine the feature value when the first image is labeled as the non-target; and
    a second hardware processor that trains the identification model through machine learning using the teacher data.

2. The ultrasound diagnostic imaging training apparatus according to claim 1, wherein
    the first hardware processor sets a region for extracting the first image in accordance with an operation performed by a user to designate the target in the ultrasound image used for training.

3. The ultrasound diagnostic imaging training apparatus according to claim 2, wherein
    the first hardware processor sets, as the region for extracting the first image, a specific region centered on a position specified by coordinates of the target designated by the user.

4. The ultrasound diagnostic imaging training apparatus according to claim 1, wherein
    the first reference data includes a likelihood distribution in which a likelihood for a region corresponding to the target is set as a maximum likelihood and a likelihood for an object located at a larger distance from the target becomes lower, and
    in the second reference data, a likelihood for a region corresponding to an entirety of the first image is 0.

5. The ultrasound diagnostic imaging training apparatus according to claim 1, wherein
    the target is a nerve, and
    the non-target includes a blood vessel.

6. The ultrasound diagnostic imaging training apparatus according to claim 1, wherein
    the first image includes a puncture needle inserted into or around a nerve.

7. The ultrasound diagnostic imaging training apparatus according to claim 1, wherein
    the first reference data is set for a plurality of the targets.

8. The ultrasound diagnostic imaging training apparatus according to claim 1, wherein
    the first hardware processor generates a plurality of sets of the teacher data from the first image.

9. The ultrasound diagnostic imaging training apparatus according to claim 8, wherein
    the first hardware processor references the reference data to calculate information relating to the likelihood of the target for the second image, and associates the feature value of the second image with a target likelihood for a pixel block at a center of the second image.

10. The ultrasound diagnostic imaging training apparatus according to claim 1, further comprising
    a storage that stores a training history of the identification model.

11. An ultrasound diagnostic imaging apparatus comprising:
    the ultrasound diagnostic imaging training apparatus according to claim 1; and
    a third hardware processor that executes the identification model and outputs the information relating to the likelihood of the target in response to an input of a diagnostic ultrasound image.

12. The ultrasound diagnostic imaging training apparatus according to claim 1, wherein
    at least the first reference data represents distribution of target likelihood in an area and is adjusted in accordance with a size of the first image, the feature value of the second image being determined from a location of the second image within the first image and the target likelihood in the preset reference data associated with the location of the second image.

13. An identification model training method for training an identification model to be used for identifying a target in an ultrasound image generated based on reflected ultrasound reflected from inside a subject, the identification model training method comprising:
    extracting a first image from the ultrasound image used for training, wherein the first image is extracted based on a user input that identifies a location of the first image in the ultrasound image and labels the first image as a target or a non-target, the preset reference data includes a first reference data that is used to determine the feature value when the first image is labeled as the target and a second reference data that is used to determine the feature value when the first image is labeled as the non-target;
    generating teacher data in which a feature value of a second image included in the first image is associated with information relating to a likelihood of the target, the generation of the teacher data being based on the first image and preset reference data; and
    training the identification model through machine learning using the teacher data.

14. A non-transitory recording medium storing a computer readable training program for training an identification model to be used for identifying a target in an ultrasound image generated based on reflected ultrasound reflected from inside a subject, the training program causing a computer to perform:

extracting a first image from the ultrasound image used for training, wherein the first image is extracted based on a user input that identifies a location of the first image in the ultrasound image and labels the first image as a target or a non-target, the preset reference data includes a first reference data that is used to determine the feature value when the first image is labeled as the target and a second reference data that is used to determine the feature value when the first image is labeled as the non-target;

generating teacher data in which a feature value of a second image included in the first image is associated with information relating to a likelihood of the target, the generation of the teacher data being based on the first image and preset reference data; and training the identification model through machine learning using the teacher data.

15. An ultrasound diagnostic apparatus for generating and displaying an ultrasound image based on reflected ultrasound reflected from inside a subject, the ultrasound diagnostic apparatus comprising:

a fourth hardware processor that generates a B-mode image, the generation of the B-mode image being based on a reception signal corresponding to the reflected ultrasound;

a fifth hardware processor that obtains information relating to a likelihood of a target in the B-mode image by using an identification model and generates a likelihood distribution for the B-mode image, the generation of the likelihood distribution being based on the information relating to the likelihood of the target, the identification model being trained in advance such that a likelihood for a region corresponding to the target becomes high and a likelihood for a structure other than the target becomes low; and a sixth hardware processor that displays a region corresponding to the target in the B-mode image in a visually recognizable manner by using the likelihood distribution.

16. The ultrasound diagnostic apparatus according to claim 15, wherein
the target is a nerve,
the structure other than the target includes a blood vessel, and
the identification model is trained in advance based on reference data including at least the nerve.

17. The ultrasound diagnostic apparatus according to claim 15, wherein
the sixth hardware processor displays the region corresponding to the target in such a manner that at least one of a hue, saturation, and lightness of the B-mode image is changed in accordance with the likelihood distribution.

18. The ultrasound diagnostic apparatus according to claim 17, wherein
the sixth hardware processor displays a non-target region in the B-mode image without a change, the non-target region being a region for which a target likelihood is lower than a predetermined threshold in the likelihood distribution.

19. The ultrasound diagnostic apparatus according to claim 15, wherein
the sixth hardware processor displays contour lines based on the likelihood distribution in such a manner as to be superimposed on the B-mode image.

20. The ultrasound diagnostic apparatus according to claim 15, wherein
the sixth hardware processor displays a target frame based on the likelihood distribution in such a manner as to be superimposed on the B-mode image.

* * * * *